United States Patent
Dorovsky (10) Patent No.: US 9,354,348 B2
(45) Date of Patent: *May 31, 2016

(54) METHOD OF MEASURING PARAMETERS OF A POROUS MEDIUM USING NANOPARTICLE INJECTION

(75) Inventor: Vitaly N. Dorovsky, Novosibirsk (RU)

(73) Assignee: BAKER HUGHES INCORPORATED, Houston, TX (US)

( * ) Notice: Subject to any disclaimer, the term of this patent is extended or adjusted under 35 U.S.C. 154(b) by 800 days.

This patent is subject to a terminal disclaimer.

(21) Appl. No.: 13/578,192

(22) PCT Filed: Sep. 21, 2011

(86) PCT No.: PCT/RU2011/000718
§ 371 (c)(1),
(2), (4) Date: Aug. 9, 2012

(87) PCT Pub. No.: WO2013/043075
PCT Pub. Date: Mar. 28, 2013

(65) Prior Publication Data
US 2013/0073208 A1    Mar. 21, 2013

(51) Int. Cl.
*G01V 3/26* (2006.01)
*G06F 19/00* (2011.01)
*E21B 49/00* (2006.01)
*G01V 3/08* (2006.01)
*G01V 3/30* (2006.01)
*G01N 15/08* (2006.01)

(52) U.S. Cl.
CPC .................. *G01V 3/26* (2013.01); *G01V 3/265* (2013.01); *E21B 49/008* (2013.01); *G01N 15/082* (2013.01); *G01V 3/08* (2013.01); *G01V 3/30* (2013.01)

(58) Field of Classification Search
CPC ........... G01V 3/26; G01V 3/265; G01V 3/30; G01V 3/08; G01V 2210/6244; G01V 2210/6246; E21B 49/008; G01N 15/082
See application file for complete search history.

(56) References Cited

U.S. PATENT DOCUMENTS

| 4,881,208 | A  | * | 11/1989 | Liu | .......................... | G01V 1/46 181/105 |
| 5,519,322 | A  | * | 5/1996  | Pozzi et al. | ................... | 324/346 |
| 7,500,539 | B1 | * | 3/2009  | Dorovsky et al. | ............. | 181/102 |

(Continued)

FOREIGN PATENT DOCUMENTS

WO    2009142779 A1    11/2009

OTHER PUBLICATIONS

Bresme et al., "Nanoparticles at fluid interfaces" J. Phys.: Condens. Matter 19 (2007) 413101 (33pp).*
Wilt et al., "Oil field reservoir characterization and monitoring using electromagnetic geophysical techniques" Journal of Petroleum Science and Engineering 39 (2003) 85-97.*

(Continued)

*Primary Examiner* — Mohamed Charioui
*Assistant Examiner* — John Kuan
(74) *Attorney, Agent, or Firm* — Cantor Colburn LLP (57) ABSTRACT

The present disclosure relates to methods and apparatuses for evaluating a porous earth formation. The method may include estimating at least one parameter of interest of the earth formation using a displacement velocity of nanoparticles injected into the porous earth formation and exposed to an alternating magnetic field. The method may include using at least one processor to estimate the value of the at least one parameter. The apparatus may include an alternating magnetic field source, nanoparticles responsive to a magnetic field, and a sensor configured to measure the motion of the nanoparticles.

10 Claims, 4 Drawing Sheets

(56) References Cited

U.S. PATENT DOCUMENTS

| | | |
|---|---|---|
| 7,710,823 B2 * | 5/2010 | Tabarovsky et al. ............ 367/35 |
| 2008/0125974 A1 * | 5/2008 | Dubinsky et al. ............... 702/11 |
| 2008/0290876 A1 * | 11/2008 | Ameen ......................... 324/346 |
| 2009/0179649 A1 * | 7/2009 | Schmidt et al. ............... 324/345 |
| 2009/0180350 A1 * | 7/2009 | Dorovsky et al. .............. 367/35 |
| 2013/0091941 A1 * | 4/2013 | Huh et al. .................. 73/152.08 |

OTHER PUBLICATIONS

Tichelaar et al., "Modeling of borehole Stoneley waves in the presence of skin effects" J. Acoust. Soc. Am. 105 (2), Pt. 1, Feb. 1999.*
International Preliminary Report on Patentability and Written Opinion for corresponding PCT/RU2011/000718, dated Mar. 25, 2014, pp. 1-5.

* cited by examiner

METHOD OF MEASURING PARAMETERS OF A POROUS MEDIUM USING NANOPARTICLE INJECTION

BACKGROUND OF THE DISCLOSURE

1. Field of the Disclosure

This disclosure generally relates to exploration and production of hydrocarbons involving investigations of regions of an earth formation penetrated by a borehole. More specifically, the disclosure relates to the characterizing the earth formation using a logging tool in the borehole.

2. Description of the Related Art

A variety of techniques are currently utilized in characterizing earth formations. These methods are designed to determine formation parameters, including, among other things, the resistivity, porosity, dielectric susceptibility, and permeability of a rock formation surrounding a borehole drilled for recovering the hydrocarbons. Electroacoustic methods for earth borehole logging are well known to persons having an ordinary level of skill in the art, and various devices and various techniques have been described for this purpose. Typically, the tools designed to provide the desired information are used to log the borehole. Much of the logging is done after the boreholes have been drilled.

Extensive work has been done in the determination of formation properties using electroacoustic methods. In an electroacoustic method, an electric field may be applied at a 90 degree angle to an interface between a porous earth formation and a borehole fluid. An alternative magnetic field may then be applied to the surface of the earth formation.

SUMMARY OF THE DISCLOSURE

In view of the foregoing, the present disclosure is directed to a method and apparatus for estimating at least one parameter of interest of an earth formation using nanoparticles injected into the earth formation and an alternating magnetic field in a borehole penetrating the earth formation.

One embodiment according to the present disclosure includes a method of estimating a value of at least one parameter of interest of an earth formation, comprising: applying an alternating magnetic field at a plurality of frequencies to an interface between the earth formation and a borehole fluid; injecting nanoparticles into the earth formation; estimating a displacement velocity of the nanoparticles using a sensor; and estimating a value of the at least one parameter of interest using the estimated displacement velocity.

Another embodiment according to the present disclosure includes a computer-readable medium product having instructions thereon that, when executed, cause at least one processor to perform a method, the method comprising: applying an alternating magnetic field at a plurality of frequencies to an interface between the earth formation and a borehole fluid; injecting nanoparticles into the earth formation; and estimating a value of at least one parameter of interest using a displacement velocity of the nanoparticle measured by a sensor.

Another embodiment according to the present disclosure includes an apparatus configured to estimate a value of at least one parameter of interest of an earth formation, comprising: a tool configured to be conveyed into a borehole; a magnet on the tool configured to apply an alternating magnetic field at a plurality of frequencies to an interface between the earth formation and a borehole fluid; a device configured to inject nanoparticles into the earth formation; a sensor configured to estimate a displacement velocity of the nanoparticles; and a processor configured to estimate the value of the at least one parameter of interest using the estimated displacement velocity.

BRIEF DESCRIPTION OF THE DRAWINGS

The present disclosure is best understood with reference to the accompanying figures in which like numerals refer to like elements and in which like numerals refer to like elements and in which.

DETAILED DESCRIPTION OF THE DISCLOSURE

In the disclosure that follows, in the interest of clarity, not all features of actual implementations are described. It will of course be appreciated that in the development of any such actual implementation, as in any such project, numerous engineering and technical decisions must be made to achieve the developers' specific goals and subgoals (e.g., compliance with system and technical constraints), which will vary from one implementation to another. Moreover, attention will necessarily be paid to proper engineering and programming practices for the environment in question. It will be appreciated that such development efforts may be complex and time-consuming, outside the knowledge base of typical laymen, but would nevertheless be a routine undertaking for those of ordinary skill in the relevant fields.

Parameters of interest of an earth formation (or other porous medium) may be estimated using nanoparticles responsive to an alternating magnetic field at a boundary (interface) between the earth formation and a downhole fluid. Parameters that may be estimated may include, but are not limited to, porosity, permeability, and dielectric susceptibility.

An electric field source may be used to apply an electric field orthogonal to the boundary and constant with respect to time. The electric field may have a galvanic nature. In the plane of the boundary, a magnetic field source may apply an alternating magnetic field to the surface. The magnetic field source may be configured to produce an alternating magnetic field over a range of frequencies.

In the same plane of the same interface, there may be a sensor configured to estimate a displacement velocity of a matrix in the direction orthogonal to the alternating magnetic field while an injector may inject nanoparticles with the spontaneous electric moment into the earth formation. The nanoparticles may have a dielectric susceptibility, κ, of about $10^3$ or greater. The sensor may be used to estimate the displacement velocity of the matrix with respect to characteristic frequencies. The sensor may be configured to estimate responses of the matrix at one or more characteristic frequencies. Illustrative embodiments of the present claimed subject matter are described in detail below.

Figure 1:
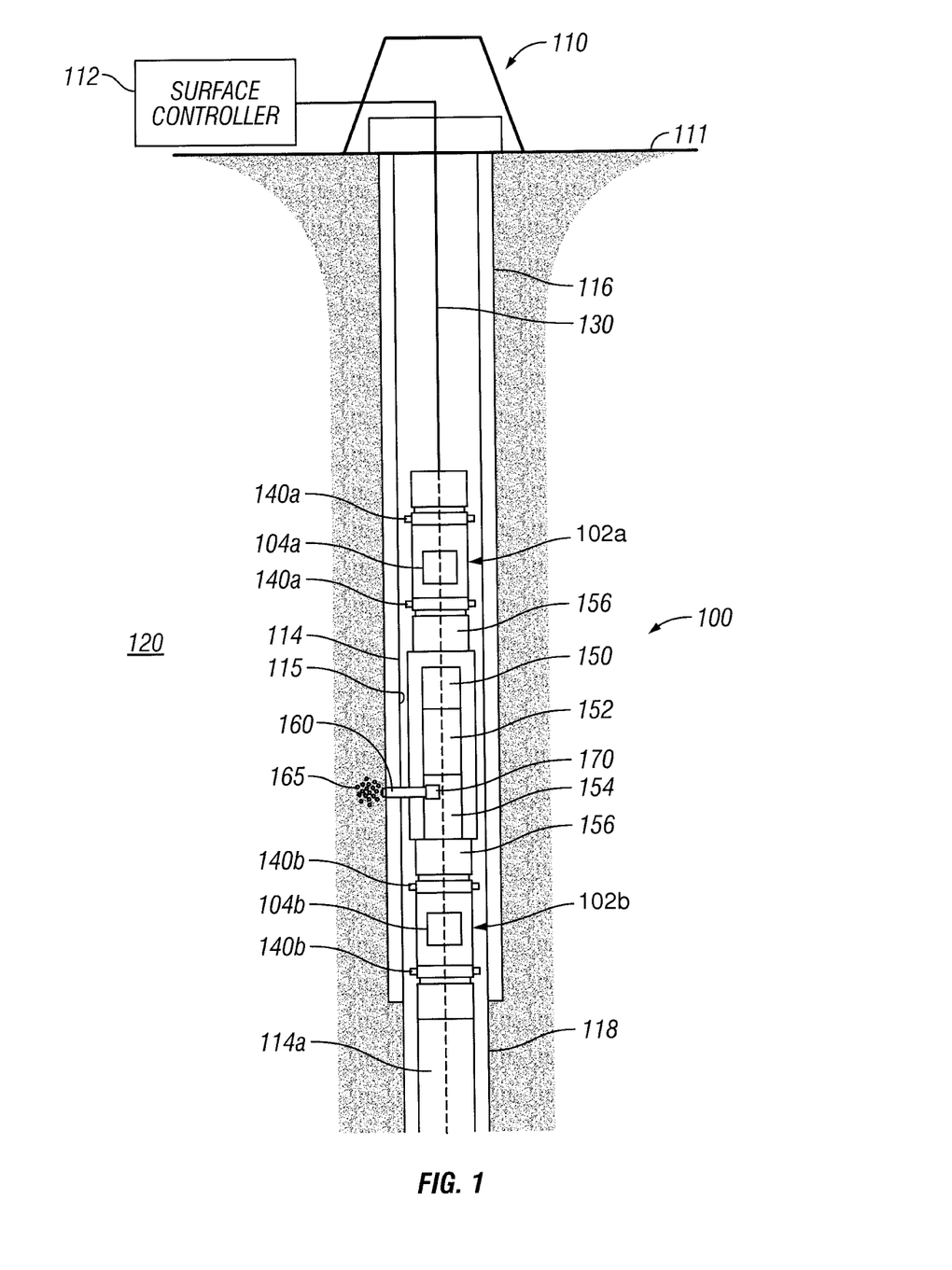
FIG. 1 is a schematic of a drilling site including an electromagnetic tool for estimating at least one parameter of interest of an earth formation according to one embodiment of the present disclosure.

FIG. 1 shows an exemplary apparatus suitable for performing the method of the present disclosure conveyed within a borehole having a casing. FIG. 1 shows a rig 110 on a surface 111 and positioned over a subterranean earth formation of interest 120. The rig 110 may be a part of a land well production/construction facility or an offshore well production/construction facility. A borehole 114 formed below the rig 110 may include a cased portion 116 and/or an open hole portion 118. In certain instances (e.g., during drilling, completion, work-over, and the like), a logging operation may be conducted to collect information relating to the earth formation 120 and/or the borehole 114. Typically, a tool system 100 may be conveyed downhole via an umbilical 130 to measure one or more parameters of interest relating to the earth formation 120, such as resistivity. The term "umbilical" as used hereinafter includes a cable, a wireline, slickline, drill pipe, coiled tubing, or other devices suitable for conveying the tool system 100 into the borehole 114. The tool system 100 may include one or more modules 102a, 102b each of which has a tool or a plurality of tools 104a, 104b adapted to perform one or more downhole tasks. The term "module" includes a device such as a sonde or sub that is suited to enclose or otherwise support a device that is to be deployed into the borehole. While two proximally positioned modules and two associated tools are shown, it should be understood that any finite number may be used.

The tool 104a may be a formation evaluation (FE) tool adapted to measure one or more parameters of interest relating to the earth formation and/or the borehole. The term formation evaluation (FE) tool encompasses measurement devices, sensors, and other like devices that, actively or passively, collect data about the various characteristics of the earth formation 120, directional sensors for providing information about the tool system 100 orientation or direction of movement, formation testing sensors for providing information about the characteristics of the reservoir fluid or for evaluating the reservoir conditions. The formation evaluation (FE) sensors may include resistivity sensors for determining the earth formation 120 resistivity or dielectric constant of the earth formation or the presence or absence of hydrocarbons; acoustic sensors for determining the acoustic porosity of the earth formation and the bed boundary in the earth formation; nuclear sensors for determining density of the earth formation, nuclear porosity and/or certain rock characteristics; or nuclear magnetic resonance (NMR) sensors for determining the porosity and/or other petrophysical characteristics of the earth formation. The direction and position sensors may include a combination of one or more accelerometers, gyroscopes, or magnetometers. The accelerometers preferably may provide measurements along three axes, in particular along three substantially mutually perpendicular axes. The formation testing sensors may collect earth formation fluid samples and determine the properties of the fluid, which may include physical or chemical properties. Pressure measurements may provide information about certain characteristics of the reservoir.

The tool system 100 may include telemetry equipment 150, a local or downhole processor or controller 152, and a downhole power supply 154. The telemetry equipment 150 may provide two-way communication for exchanging data signals between a surface controller or processor 112 and the tool system, as well as for transmitting control signals from the surface controller to the tool system.

A first module 102a may include a first tool 104a configured to measure a first parameter of interest and a second module 102b may include a second tool 104b that is configured to measure a second parameter of interest. In order to execute their assigned tasks, the first tool and the second tool may be in different positions. The positions can be with reference to an object such as the borehole 114, a borehole wall 115, or other proximally positioned tooling. The term "position" may be understood to encompass a radial position, an inclination, and/or an azimuthal orientation. In the illustration of FIG. 1, the longitudinal axis 114a of the borehole ("the borehole axis") is used as a reference axis to describe the relative radial positioning of the tools 104a, 104b. Other objects or points may also be used as a reference frame against which movement or position can be described. Moreover, the tasks of the tools may change during a borehole-related operation. Generally speaking, the tool may be adapted to execute a selected task based on one or more selected factors. These factors may include, but may not be limited to depth, time, changes in earth formation characteristics, and/or the changes in tasks of other tools.

In an exemplary embodiment, the modules 102a and 102b may each be provided with positioning devices 140a, 140b, respectively, which are configured to maintain the respective modules 102a, 102b at selected radial positions relative to a reference position (e.g., the borehole axis 114a). The positioning devices may also adjust the radial positions of the respective modules upon receiving one or more surface command signals or automatically in a closed-loop type manner. These selected radial positions may be maintained or adjusted independently of the radial position(s) of an adjacent downhole device (e.g., measurement tools, sonde, module, sub, or other like equipment). An articulated member, such a flexible joint 156 that couples the respective modules to the tool system 100 may provide a degree of bending or pivoting to accommodate the radial positioning differences between adjacent modules or other equipment (for example, a processor sonde). One or more of the positioning devices may have fixed positioning members.

The tool 100 may include an injector 160 configured to move nanoparticles 165 from storage 170 in the tool to the earth formation 120. The nanoparticles 165 may be responsive to magnetic fields. The nanoparticles 165 may have a spontaneous electric moment. The nanoparticles 165 may accumulate at an interface 301 (FIG. 3).

Figure 2A:
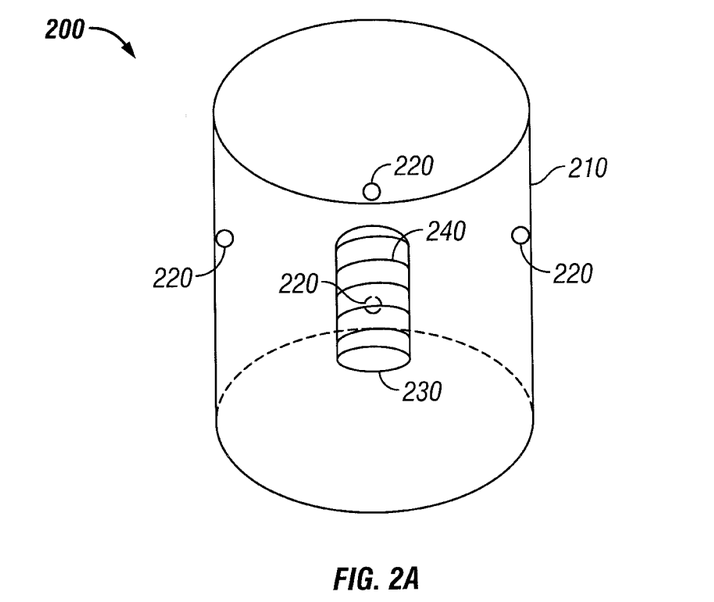
FIG. 2A is a schematic view of a magnet configuration for the electromagnetic tool in accordance with one embodiment of the present disclosure.
Figure 2B:
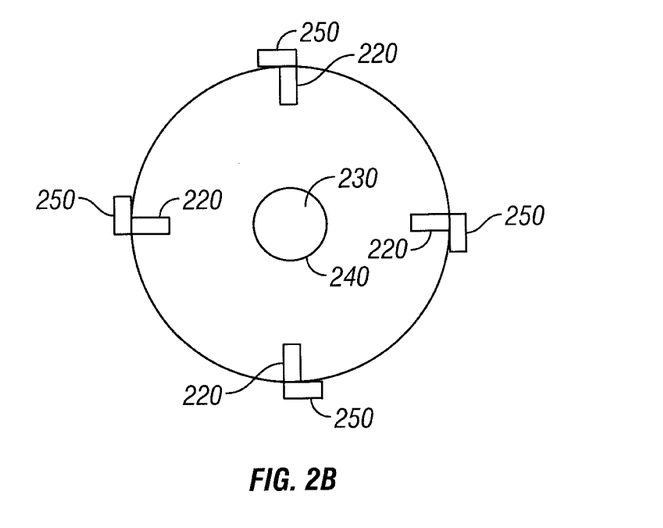
FIG. 2B is a top view of a schematic of an electromagnetic tool suitable for use with the present disclosure.

FIGS. 2A and 2B illustrate an electromagnetic tool 200 that may be included in tool 100. Electromagnetic tool 200 may include a housing 210 with one or more electrodes 220 configured to generate an electric field substantially orthogonal to the boundary layer 301. Electromagnetic tool 200 may also include a magnetic core 230 that may be wrapped, at least in part, by a coil 240. The magnetic core 230 may include two or more sections (not shown). The magnetic core 230 and coil 240 may be configured to generate an alternating magnetic field in a direction substantially parallel the borehole axis 114a. One or more sensors 250 may be disposed on the housing 210 and configured to estimate a displacement velocity of nanoparticles 165 in the earth formation 120. In some embodiments, the sensors 250 may be positioned in contact with the boundary layer/interface 301.

Figure 3:
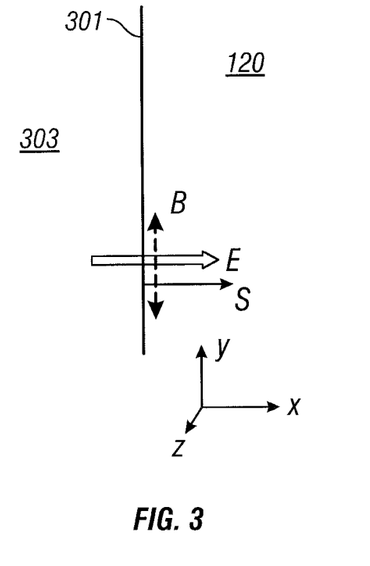
FIG. 3 schematically illustrates the coordinate system used in the discussion herein.

Turning now to FIG. 3, the coordinate system use in the discussion below is shown. Interface 301 is shown between a fluid field borehole 303 and porous earth formation 120. A static electric field E may be applied normal to the interface 301. An alternating magnetic field B is applied with a component parallel to the interface 301.

Figure 4:
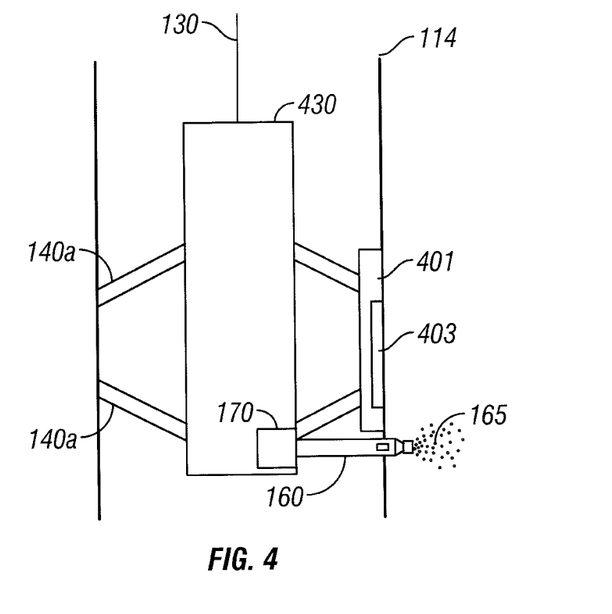
FIG. 4 is a schematic of an embodiment of the electromagnetic tool with pad-mounted sensors according to the present disclosure.

A simple wireline implementation is illustrated in FIG. 4. Shown therein is a logging tool 430 with sensor assembly 403 on a pad 401. The sensor assembly 403 may include one or more sensors 250. Also shown is an injector 160 for nanoparticles 165. The injector 160 may be located near or adjacent to the pad 401 or may be included as part of the pad 401. An MWD (measurement-while-drilling) implementation (not shown) may have sensors mounted on stabilizers.

Figure 5:
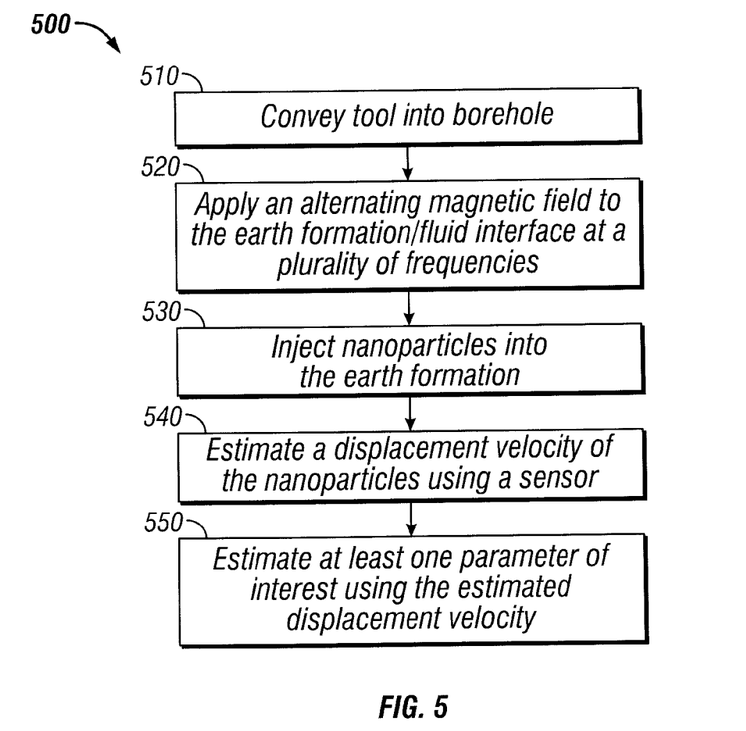
FIG. 5 is a flow chart for a method for one embodiment according to the present disclosure.

Embodiments of the apparatus according to the present disclosure may be used to perform a method. FIG. 5 shows a flow chart for one embodiment of the method 500. In step 510, the tool 100 may be conveyed in borehole 114. In step 520, an alternating magnetic field may be applied by tool 100 to the interface 301 (approximately borehole wall 115) between the earth formation 120 and a downhole fluid in the borehole 114. In step 530, nanoparticles 165 may be injected into the earth formation 120. In step 540, a sensor 250 may be used to estimate a displacement velocity of the nanoparticles 165. In step 550, at least one parameter of interest of the earth formation 120 may be estimated using the estimated displacement velocity of the nanoparticles 165. In some embodiments, the characteristic frequency of the downhole fluid at the interface with the earth formation 120 may be estimated.

The theoretical basis for the method may include filtration theory for describing motion in electrically polarized weakly conducting fluid (electrolyte) through a deforming elastic porous skeleton. Assuming insignificant dispersion effects, the theoretical basis can be expressed via the following set of equations:

$$\frac{\partial \rho}{\partial t} + div \quad j = 0 \tag{1}$$

$$\frac{\partial S}{\partial t} + div\left(S\frac{j}{\rho} + \frac{q}{T}\right) = \frac{R}{T},$$

$$R = -(j - \rho u)f^\partial + i_0\left[E + \frac{v \wedge B}{c_e}\right] - q\frac{\nabla T}{T},$$

$$\frac{\partial g_{ik}}{\partial t} + g_{jk}\partial_i u_j + g_{ij}\partial_k u_j + u_j\partial_j g_{ik} = 0.$$

$$\frac{\partial v}{\partial t} + (v, \nabla)v = -\frac{\nabla p}{\rho} + \frac{\rho_s}{2\rho}\nabla(u-v)^2 - \frac{h_{\mu\nu}}{2\rho}\nabla g_{\mu\nu} +$$

$$\frac{1}{\rho}\frac{\partial}{\partial t}\frac{P \wedge B}{c_e} + \frac{1}{\rho}\partial_k\left(j_k\frac{P \wedge B}{c_e}\right) + \frac{P\nabla B}{\rho} + \frac{j^e \wedge B}{\rho_l c_e} + f^\partial,$$

$$\frac{\partial u_i}{\partial t} + (u, \nabla)u_i = -\frac{\partial_i p}{\rho} - \frac{\rho_l}{2\rho}\partial_i(u-v)^2 + \frac{\rho_l}{2\rho\rho_s}h_{\mu\nu}\partial_i g_{\mu\nu} -$$

$$\frac{1}{\rho_s}\partial_\mu(h_{\mu\nu}g_{i\nu}) + \frac{1}{\rho}\frac{\partial}{\partial t}\frac{(P \wedge B)_i}{c_e} + \frac{1}{\rho}\partial_k\left(j_k\frac{(P \wedge B)_i}{c_e}\right) + \frac{P\partial_i E}{\rho} - \frac{\rho_l}{\rho_s}f_i^\partial.$$

where, $j=j_0+\rho v$ is the relationship between the momentum and its invariant part $j_0$, $i_0=j^e-\chi_s u+\chi_l v$, $g_{ik}$ is the metric deformation tensor, t is time, T is temperature, $\mu'$ is the chemical potential, S is the entropy of the unit volume, $E_0$ is the internal energy of the unit volume identifying the medium by this First Principle of Thermodynamics:

$$dE_0 = TdS + \mu'd\rho + (u-v)dj_0 + \frac{h_{ik}}{2}dg_{ik} + \left(E + \frac{j \wedge B}{\rho c_e}\right)dP - \frac{j \wedge P}{\rho c_e}dB \tag{2}$$

where $\rho=\rho_l+\rho_s$ is density of the medium (matrix+liquid) $\rho_s$ is partial density of the containing porous matrix, $\rho_l$ is partial density of the saturating fluid continuum, v is the velocity of the hydrodynamic flow of fluid, p is pressure associated with the state equations and chemical potentials through the formula $$p = -E_0 + TS + \rho\left[\mu' - \frac{j(P \wedge B)}{\rho^2 c_e}\right] + EP + (u-v)j^0, \tag{3}$$

where u is the velocity of elastic deformation of the containing porous matrix, E is the electric field, B is the magnetic field, P is electric polarization, and $c_e$ is the velocity of light.

The system closes by linear dissipative equations:

$$f^\partial = \chi(\rho u - j) + \alpha\left[E + \frac{v \wedge B}{c_e}\right] + \alpha_{13}\frac{\nabla T}{T}, \tag{4}$$

$$j^e = \alpha(\rho u - j) + \sigma\left[E + \frac{v \wedge B}{c_e}\right] + \alpha_{23}\frac{\nabla T}{T},$$

$$q = \alpha_{13}(\rho u - j) + \alpha_{23}\left[E + \frac{v \wedge B}{c_e}\right] + \kappa\frac{\nabla T}{T},$$

($\chi$, $\alpha_{13}$, $\kappa$, $\alpha_{23}$, $\alpha$ are kinetic coefficients) and electrodynamic equations $$rotE = -\frac{1}{c_e}\frac{\partial B}{\partial t}, \quad rotB = \frac{4\pi}{c_e}j^e + \frac{1}{c_e}\frac{\partial D}{\partial t}, \quad divD = 4\pi\chi, \quad divB = 0. \tag{5}$$

Here $j_e$ is the electric current. Full energy is related to the internal energy via the following equation:

$$E = E_0 + j_0 v + \frac{\rho v^2}{2} + \frac{E^2 + B^2}{8\pi}, \tag{6}$$

In these equations, the terms with bulk free charges are left out; and it is assumed that the matrix containing the electrolyte has zero conductivity. Through these calculations, an acoustic response of the electrolyte-saturated porous medium to the inductive electromagnetic impact in the presence of the longitudinal electric current of galvanic nature may be obtained.

A porous medium, such as an earth formation with a porous lithology, may be treated as a porous half-space located along the axis x, (x>0) and separated from a fluid by the plane (y, z, x=0). An electromagnetic field in the porous medium may be excited by the alternating magnetic field B=(0, $B_y$(t), 0) applied to the surface of the interface between the two media (y, z, x=0) such that an acoustic response may be obtained. The parameters of interest of the earth formation may be estimated using the acoustic response u=(0, 0, $u_z$(t)) of the system on the surface (y, z, x=0) in the presence of the longitudinal electric current j=($j_x^{(0)}$, 0, 0) of galvanic nature. The electromagnetoacoustic equations for the electrically polarized medium given above in their linearized form for the shear oscillation modes may be simplified in the acoustic approximation:

$$\ddot{u}_z - c_t^2 \frac{\partial^2 u_z}{\partial x^2} + \frac{\rho_l^2}{\rho_s}\chi(\dot{u}_z - \dot{v}_z) - \frac{\kappa E_x^{(0)}}{\rho}\frac{\partial E_z}{\partial x} = 0, \quad (7)$$

$$\ddot{v}_z - \rho_l^2\chi(\dot{u}_z - \dot{v}_z) - \frac{\kappa E_x^{(0)}}{\rho}\frac{\partial \dot{E}_z}{\partial x} - \frac{\sigma E_x^{(0)}}{\rho_l}\frac{\partial E_z}{\partial x} = 0,$$

$$\frac{\partial E_z}{\partial x} = \frac{1}{c_e}\frac{\partial B_y}{\partial t}, \frac{4\pi\sigma}{c_e}E_z = \frac{\partial B_y}{\partial x}.$$

where $\kappa$ is the dielectric susceptibility. For harmonic amplitudes, the expression:

$$(u,v,E_z,B_y) \Rightarrow (u,v,E_z,B_y) \cdot \exp(-i\omega t) \quad (8)$$

may be used. These equations may lead to:

$$\frac{\partial^2 u_z}{\partial x^2} - P^2 u_z = -i\frac{\kappa P^2}{\rho\omega}E_x^{(0)}\frac{\partial E_z}{\partial x} - \frac{\sigma}{\rho_s c_t^2}\frac{\overline{\omega}}{\overline{\omega}-i\omega}E_x^{(0)}\frac{\partial E_Z}{\partial x}, \quad (9)$$

$$P = i\frac{\omega}{c_t}\sqrt{1 + \frac{\rho_l}{\rho_s}\frac{\overline{\omega}}{\overline{\omega}-i\omega}}$$

$$\frac{\partial^2 E_z}{\partial x^2} - i\frac{4\pi\sigma\omega}{c^2}E_z = 0$$

The solution may apply for amplitudes evanescent at infinity and a stress-free boundary:

$$u_z = \quad (10)$$

$$\frac{P^2}{P^2-Q^2}\cdot\left(\frac{e^{Q\cdot x}}{Q} - \frac{e^{P\cdot x}}{P}\right)\cdot\frac{E_x^{(0)}B_y(\omega)|_{x=0}}{c_e\rho}\cdot\left[\kappa - i\frac{\sigma\rho}{P^2 c_t^2 \rho_s}\cdot\frac{\omega\overline{\omega}}{\overline{\omega}-i\omega}\right]$$

$$E_z = -\frac{i\omega}{cQ}\cdot B_y(\omega)\Big|_{x=0}e^{Q\cdot x}, Q = \frac{i-1}{c_e}\sqrt{\pi\sigma\omega}.$$

The amplitude of the response at the interface may be represented by the following expression:

$$u_z|_{x=0} = \frac{P(\omega)}{P(\omega)-Q(\omega)}\cdot \quad (11)$$

$$\frac{E_x^{(0)}B_y(\omega)|_{x=0}}{\rho c_e}\cdot\left[\left(\kappa - \frac{\rho}{\rho_s}\frac{\sigma\overline{\omega}}{\omega^2+\rho^2\overline{\omega}^2/\rho_s^2}\right) + i\frac{\rho^2}{\rho_s^2}\frac{\sigma\overline{\omega}/\omega}{\omega^2+\rho^2\overline{\omega}^2/\rho_s^2}\right].$$

Figure 6:
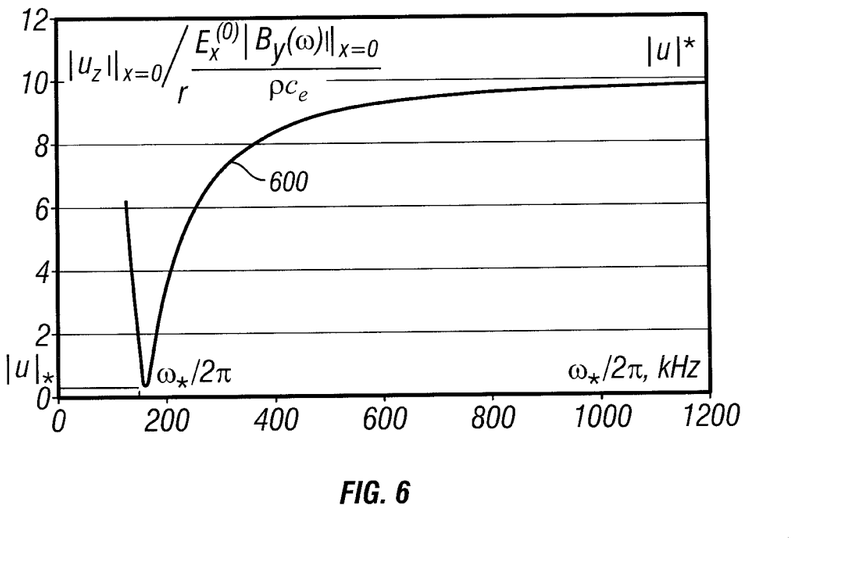
FIG. 6 is a graph of a function modulus without nanoparticles of one embodiment according to the present disclosure.

FIG. 6 shows a graph with curve 600, which represent a function modulus $|u_z||_{x=0}$ as a frequency function measured in terms of the units of $\lambda=E_x^{(0)}|B_y(\omega)||_{x=0}/\rho c_e$, which is dimensionless.

$$|u_z||_{x=0}/\lambda = \quad (12)$$

$$\left|\frac{P(\omega)}{P(\omega)-Q(\omega)}\right|\sqrt{\left(\kappa - \frac{\rho}{\rho_s}\frac{\sigma\overline{\omega}}{\omega^2+\rho^2\overline{\omega}^2/\rho_s^2}\right)^2 + i\frac{\rho^4}{\rho_s^4}\frac{\sigma^2\overline{\omega}^4/\omega^2}{(\omega^2+\rho^2\overline{\omega}^2/\rho_s^2)^2}}.$$

Having measured the asymptomatic value of this modulus, $$u_z^*|_{x=0} = \frac{E_x^{(0)}B_y(\omega)|_{x=0}}{\rho c_e}\cdot\kappa, \quad (13)$$

and dielectric susceptibility may be estimated using the expression:

$$\kappa = |u_z^*|\Big|_{x=0}\Bigg/\frac{E_x^{(0)}B_y(\omega)|_{x=0}}{\rho c_e} \quad (14)$$

of the medium for given amplitudes of the electromagnetic fields and density of the medium. The characteristic frequency $\omega_*$ may be determined as follows:

$$\omega_* = \sqrt{\frac{\sigma}{\rho-\rho_l}*\frac{\eta}{\kappa*k}} \quad (15)$$

Here the relationship between the frequency $\overline{\omega}$ and permeability k is used: $\overline{\omega}=\rho_l\chi=\rho_l\eta/\rho\rho_l k=\eta/\rho k$. The measured acoustic response $u_*|_{x=0}$ at characteristic frequency $\omega_*$ may lead to an expression of the relationship between the constants of the porous medium.

$$(u_*|_{x=0}) = \lambda\left(\frac{\rho\overline{\omega}}{\rho_s\sigma}\right)^{\frac{1}{2}}\cdot\kappa^{\frac{3}{2}} \quad (16)$$

These equations may allow determination of the physical parameters of the porous medium from three measured values $(|u_z^*||_{x=0}, \omega_*, u_*|_{x=0})$.

For example, dielectric susceptibility, permeability, and conductivity may be calculated as follows:

$$\kappa = u_z^*|_{x=0}/\lambda, \frac{\rho\overline{\omega}}{\rho_s} = \frac{\omega_*|u|_*}{\lambda\cdot\kappa}, \sigma = \frac{\kappa\cdot\omega_*^2}{\rho\overline{\omega}/\rho_s}, \quad (17)$$

where fluid viscosity $\eta$, electric conductivity $\sigma$, density $\rho$, and fluid densities, $\rho_s$ are known.

Figure 7:
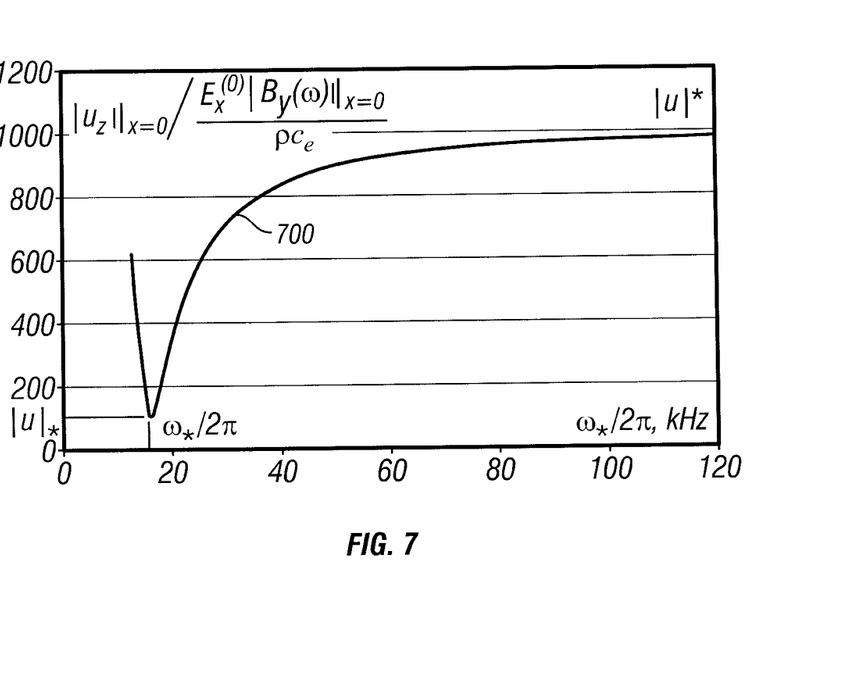
FIG. 7 is a graph of a function modulus with nanoparticles of one embodiment according to the present disclosure.

For example, using an electric current density of a 5 a/cm² of galvanic nature and conductivity $\sigma=10^9$ 1/s may provide the electric field of $E_x^{(0)}=15$ statV/cm. Also using a magnetic field of $B_y(\omega)=10^3$ Gs. Then, for density 3.0 g/cm³ and susceptibility 10, the response amplitude of $|u|*=1.6\cdot10^{-6}$ sm/s, $|u|_*=1.6\cdot10^{-8}$ sm/s for the asymptotic value of the frequency may be obtained. The characteristic frequency here is $\omega_*\approx170$ kHz (see FIG. 6). The amplitude at 170 kHz may be so small as to reduce the likelihood of obtaining reliable estimates for the parameters of interest. However, an injection of dielectric nanoparticles 165 with the spontaneous electric moment may improve the quality for estimates of parameters of interest. The injection of the nanoparticles 165 may increase the value of the dielectric susceptibility such that $\kappa=10^3$. The value of the corresponding acoustic response is shown in FIG. 7 as curve 700. Curve 700 shows the function modulus, $|u_z||_{x=0}$, which is indicative of the displacement velocity of the nanoparticles 165.

In the presence of the nanoparticles 165, the characteristic frequency $\omega_*\approx16$ kHz has substantially decreased, $|u|*=1.6\cdot10^{-5}$ sm/s, $|u|_*=1.6\cdot10^{-4}$ sm/s. The response amplitude $u_*|_{x=0}$ may also increase. As shown in FIG. 7, the response amplitude has increased by about 100 times.

Implicit in the processing of the data is the use of a computer program implemented on a suitable machine readable medium that enables the processor to perform the control and processing. The machine readable medium may include ROMs, EPROMs, EAROMs, Flash Memories and Optical disks. The determined formation permeabilities may be recorded on a suitable medium and used for subsequent processing upon retrieval of the BHA (bottomhole assembly). The determined formation permeabilities may further be telemetered uphole for display and analysis.

As described herein, the method in accordance with the presently disclosed embodiment of the disclosure involves several computational steps. As would be apparent by persons of ordinary skill, these steps may be performed by computational means such as a computer, or may be performed manually by an analyst, or by some combination thereof. As an example, where the disclosed embodiment calls for selection of measured values having certain characteristics, it would be apparent to those of ordinary skill in the art that such comparison could be performed based upon a subjective assessment by an analyst or by computational assessment by a computer system properly programmed to perform such a function. To the extent that the present disclosure is implemented utilizing computer equipment to perform one or more functions, it is believed that programming computer equipment to perform these steps would be a matter of routine engineering to persons of ordinary skill in the art having the benefit of the present disclosure.

Implicit in the processing of the acquired data is the use of a computer program implemented on a suitable computational platform (dedicated or general purpose) and embodied in a suitable machine readable medium that enables the processor to perform the control and processing. The term "processor" as used in the present disclosure is intended to encompass such devices as microcontrollers, microprocessors, field-programmable gate arrays (FPGAs) and the storage medium may include ROM, RAM, EPROM, EAROM, solid-state disk, optical media, magnetic media and other media and/or storage mechanisms as may be deemed appropriate. As discussed above, processing and control functions may be performed downhole, at the surface, or in both locations.

Although a specific embodiment of the disclosure as well as possible variants and alternatives thereof have been described and/or suggested herein, it is to be understood that the present disclosure is intended to teach, suggest, and illustrate various features and aspects of the disclosure, but is not intended to be limiting with respect to the scope of the disclosure, as defined exclusively in and by the claims, which follow.

While the foregoing disclosure is directed to the specific embodiments of the disclosure, various modifications will be apparent to those skilled in the art. It is intended that all such variations within the scope of the appended claims be embraced by the foregoing disclosure.

The invention claimed is:

1. A method of estimating a value of at least one parameter of interest of an earth formation, comprising:
    applying an alternating magnetic field at a plurality of frequencies to an interface between the earth formation and a borehole fluid using a magnet disposed on a tool configured to be conveyed through a borehole penetrating the earth formation;
    injecting nanoparticles into the earth formation using an injector device disposed on the tool;
    estimating a displacement velocity of the nanoparticles using a sensor disposed on the tool; and
    estimating a value of the at least one parameter of interest using the estimated displacement velocity;
    wherein estimating the value of the at least one parameter of interest further comprises estimating a characteristic frequency defined by the formula $$\omega_* = \sqrt{\frac{\sigma}{\rho - \rho_l} * \frac{\eta}{\kappa * k}},$$

where k is the permeability of the earth formation, $\kappa$ is a kinetic coefficient, $\sigma$ is electrical conductivity, $\rho$ is density of a continuum $\rho_l$ is partial density of a saturated fluid continuum, and $\eta$ is fluid viscosity.

2. The method of claim 1, wherein the at least one parameter of interest includes at least one of: (i) porosity, (ii) permeability, and (iii) dielectric susceptibility.

3. The method of claim 1, the nanoparticles being responsive to the alternating magnetic field.

4. The method according to claim 1, further comprising moving the nanoparticles from storage to the device.

5. A non-transitory computer-readable medium product having instructions thereon that, when executed, cause at least one processor to perform a method, the method comprising:
    applying an alternating magnetic field at a plurality of frequencies to an interface between the earth formation and a borehole fluid using a magnet disposed on a tool configured to be conveyed through a borehole penetrating the earth formation;
    injecting nanoparticles into the earth formation using an injector device disposed on the tool; and
    estimating a value of at least one parameter of interest using a displacement velocity of the nanoparticle measured by a sensor disposed on the tool;
    wherein estimating the value of the at least one parameter of interest further comprises estimating a characteristic frequency defined by the formula:

$$\omega_* = \sqrt{\frac{\sigma}{\rho - \rho_l} * \frac{\eta}{\kappa * k}},$$

where k is the permeability of the earth formation, $\kappa$ is a kinetic coefficient, $\sigma$ is electrical conductivity, $\rho$ is density of a continuum; $\rho_l$ is partial density of a saturated fluid continuum, and $\eta$ is fluid viscosity.

6. The non-transitory computer-readable medium product of claim 5 further comprising at least one of: (i) a ROM, (ii) an EPROM, (iii) an EEPROM, (iv) a flash memory, or (v) an optical disk.

7. An apparatus configured to estimate a value of at least one parameter of interest of an earth formation, comprising:
    a tool configured to be conveyed into a borehole penetrating the earth formation;
    a magnet on the tool configured to apply an alternating magnetic field at a plurality of frequencies to an interface between the earth formation and a borehole fluid;
    a device disposed on the tool and configured to inject nanoparticles into the earth formation;
    a sensor disposed on the tool and configured to estimate a displacement velocity of the nanoparticles; and
    a processor configured to estimate the value of the at least one parameter of interest using the estimated displacement velocity;
    wherein the processor is further configured to estimate the at least one parameter of interest by estimating a characteristic frequency defined by the formula $$\omega_* = \sqrt{\frac{\sigma}{\rho - \rho_l} * \frac{\eta}{\kappa * k}},$$

where k is the permeability of the earth formation, κ is a kinetic coefficient, σ is electrical conductivity, ρ is density of a continuum $\rho_l$ is partial density of a saturated fluid continuum, and η is fluid viscosity.

8. The apparatus of claim 7, wherein the at least one parameter of interest estimated by the processor includes at least one of: (i) porosity, (ii) permeability, and (iii) dielectric susceptibility.

9. The apparatus of claim 7, the nanoparticles being responsive to the alternating magnetic field.

10. The apparatus of claim 7, further comprising a storage device configured to store the nanoparticles.

* * * * *